United States Patent
Lu et al.

(10) Patent No.: US 10,053,666 B2
(45) Date of Patent: Aug. 21, 2018

(54) MEDIUM FOR PREPARING A NEURAL CELL AND USAGE THEREOF

(71) Applicant: SHENZHEN CELL INSPIRE BIOTECHNOLOGY CO., LTD., Shenzhen (CN)

(72) Inventors: Xiaohua Lu, Shenzhen (CN); Jiayin Yang, Shenzhen (CN); Bo Yang, Shenzhen (CN)

(73) Assignee: SHENZHEN CELL INSPIRE BIOTECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 15/026,117

(22) PCT Filed: Sep. 29, 2014

(86) PCT No.: PCT/CN2014/087828
§ 371 (c)(1),
(2) Date: Mar. 30, 2016

(87) PCT Pub. No.: WO2016/015378
PCT Pub. Date: Feb. 4, 2016

(65) Prior Publication Data
US 2016/0244720 A1    Aug. 25, 2016

(30) Foreign Application Priority Data

Jul. 29, 2014  (CN) .......................... 2014 1 0367556

(51) Int. Cl.
*C12N 5/079* (2010.01)
*A61K 35/30* (2015.01)
*C12N 5/0793* (2010.01)
*A61K 45/06* (2006.01)
*A61K 31/436* (2006.01)
*A61K 31/203* (2006.01)
*A61K 31/366* (2006.01)
*A61K 31/4409* (2006.01)
*A61K 31/506* (2006.01)
*A61K 31/5377* (2006.01)

(52) U.S. Cl.
CPC .......... *C12N 5/0619* (2013.01); *A61K 31/203* (2013.01); *A61K 31/366* (2013.01); *A61K 31/436* (2013.01); *A61K 31/4409* (2013.01); *A61K 31/506* (2013.01); *A61K 31/5377* (2013.01); *A61K 35/30* (2013.01); *A61K 45/06* (2013.01); *C12N 2500/32* (2013.01); *C12N 2500/38* (2013.01); *C12N 2501/01* (2013.01); *C12N 2501/105* (2013.01); *C12N 2501/115* (2013.01); *C12N 2501/13* (2013.01); *C12N 2501/135* (2013.01); *C12N 2501/375* (2013.01); *C12N 2501/385* (2013.01); *C12N 2501/41* (2013.01); *C12N 2501/727* (2013.01); *C12N 2501/998* (2013.01); *C12N 2506/1307* (2013.01)

(58) Field of Classification Search
None
See application file for complete search history.

(56) References Cited

U.S. PATENT DOCUMENTS

| | | |
|---|---|---|
| 2012/0021519 A1 | 1/2012 | Ichida et al. |
| 2014/0051171 A1 | 2/2014 | Christensen et al. |
| 2015/0030570 A1 | 1/2015 | Pan et al. |
| 2016/0075994 A1 | 3/2016 | Tesar et al. |

FOREIGN PATENT DOCUMENTS

| | | |
|---|---|---|
| CN | 101410510 A | 4/2009 |
| CN | 101765657 A | 6/2010 |
| CN | 103068974 A | 4/2013 |
| KR | 101213279 B1 | 12/2012 |
| KR | 20130085767 A | 7/2013 |
| WO | 2012/096705 A1 | 7/2012 |
| WO | 2014/082096 A1 | 5/2014 |
| WO | 2015/131788 A1 | 9/2015 |

OTHER PUBLICATIONS

Takahashi et al., "Retinoic acid and neurotrophins collaborate to regulate neurogenesis in adult-derived neural stem cell cultures", Journal of Neurobiology 1999, vol. 38, pp. 65-81.*

El-Akabawy et al., "Purmorphamine Increases DARPP-32 Differentiation in Human Striatal Neural Stem Cells Through the Hedgehog Pathway", Stem Cells and Development 2011, vol. 20, pp. 1873-1887.*

Peng, T., et al., Feasability of fasudil hydrochloride inducing rat bone marrow mesenchymal stem cells to differentiate into neuron-like cells, Journal of Zhengzhou University (Medical Sciences), Jul. 2010, vol. 45, No. 4, pp. 559-562.

Wang, X., et al., 蛋白酶抑制剂 MG132 在联合 NGF 诱导 PC12 细胞分化过程中的作用及机制 (The role and mechanism of protease ihibitor MG132 in the differentiation of PCT12 cells induced by NGF), Chinese Journal of Laboratory Diagnosis, Nov. 2011, vol. 15, No. 11, pp. 1819-1822.

Lingor, P., et al., Inhibition of Rho kinase (ROCK) increases neurite outgrowth on chondroitin sulphate proteoglycan in vitro and axonal regeneration in the adult optic nerve in vivo, Journal of Neurochemistry, Jun. 9, 2007, vol. 103, No. 1, pp. 181-189.

Kubo, R., et al., Rho-ROCK Inhibitors as Emerging Strategies to Promote Nerve Regeneration, Current Pharmaceutical Design, Aug. 2007, vol. 13, No. 24, pp. 2493-2499.

Wattanapanitch M., et al., Dual Small-Molecule Targeting of SMAD Signaling Stimulates Human Induced Pluripotent Stem Cells toward Neural Lineages, PLOS One, Sep. 10, 2014, vol. 9, No. 9, p. e106952.

Ladewig, J., et al., Small molecules enable highly efficient neuronal conversion of human fibroblasts, Nature Methods, Jun. 30, 2012, vol. 9, No. 6, pp. 575-578.

(Continued)

Primary Examiner — Michelle F. Paguio Frising
(74) Attorney, Agent, or Firm — Hodgson Russ LLP

(57) ABSTRACT

Usage of a protein kinase inhibitor in preparing a neural cell from a differentiated non-neural cell is provided.

8 Claims, 6 Drawing Sheets

(56) References Cited

OTHER PUBLICATIONS

Wang, C.H., et al., The role of RhoA kinase inhibition in human placenta-derived multipotent cells on neural phenotype and cell survival, Biomaterials, Feb. 12, 2013, vol. 34, No. 13, pp. 3223-3030.
Dhara, S.K., et al., Neural differentiation of human embryonic stem cells, Journal of Cellular Biochemistry, Oct. 15, 2008, vol. 105, No. 3, pp. 633-640.
Jung, D.W., et al., Reprogram or Reboot: Small Molecule Approaches for the Production of Induced Pluripotent Stem Cells and Direct Cell Reprogramming, ACS Chemical Biology, Jan. 17, 2014, vol. 9, No. 1, pp. 80-95.
The Patent Office of the Peoples Republic of China, Decision of Rejection for CN201410367556.4, May 27, 2017, 6 pages.
The Patent Office of the Peoples Republic of China, Decision of Reexamination for CN201410367556.4, Sep. 1, 2017, 1 page.

\* cited by examiner

MEDIUM FOR PREPARING A NEURAL CELL AND USAGE THEREOF

RELATED APPLICATIONS

This application is a national phase entry under 35 USC § 371 of International Application PCT/CN2014/087828 filed on Sep. 29, 2014, which claims priority to Chinese Patent Application Serial No. 201410367556.4, filed with the State Intellectual Property Office of P. R. China on Jul. 29, 2014, the entire contents of which are incorporated herein by reference.

FIELD

The present disclosure relates to biomedical field, particularly to medium for preparing a neural cell and usage thereof, more particularly to usage of a protein kinase inhibitor in preparing a neural cell from a differentiated non-neural cell, a method for preparing a neural cell, a kit for preparing neural cell, usage of a kit for preparing neural cell, a kind of neural cell or their derivative, usage of a kind of neural cell or their derivative in preparing drug for the treatment of central nervous system disorder and spinal cord injury.

BACKGROUND

Central nervous system (CNS) disorders, such as Alzheimer's Disease (AD), Parkinsin's Disease (PD), Amyotrophic Lateral Sclerosis (ALS), Multiple Sclerosis (MS), and Leukodystrophies, affect millions of people worldwide and most of CNS diseases currently have no cure. Transplantation of neural cells has been demonstrated in non-human primates and rodents to be a very promising therapeutic strategy for treating CNS disorders. However, cell therapy requires high quality and large quantities of primary neural cells that are not readily obtainable. Different methods have been developed during last two decades to produce neural cells in vitro. These technologies include generation of neural cells from human embryonic stem cells (hESC), from induced human pluripotent stem cells (hiPSC), and from direct conversion of somatic cells. There are several limitations to existing art. For example, neural cells derived from hESC encounter the safety issue due to potential tumorgenesis caused by residual hESC in the differentiated products as well as immune rejection issue due to allogeneic transplantation. hiPSC can be obtained from specific patients and thus alleviate the immunorejection issue, but like hESC, it still encounters the safety issue.

Recently, the field of direct somatic lineage conversion has attracted much attention. In 2010, Wernig's group first demonstrated that a set of transcription factors can convert fibroblasts into neurons. Several laboratories have used various neural factors and microRNAs to generate fibroblast-neuron conversion. Very recently, it was reported that over-expression transcription factors can mediate reprogramming of mouse fibroblasts to myelinogenic OPCs. Thus, direct fibroblast-OPC conversion provides an alternative, potentially complementary, tool to many of the proposed applications of hESC/hiPSC technology for both disease modeling and development of cell-based therapies. Direct conversion or reprogramming has a number of advantages, including: the time required to generate, expand and differentiate pluripotent cells is avoided, and the postmitotic state of induced neural cells has a much lower risk of cancer and teratoma formation. Therefore, neural cells derived from direct conversion of fibroblasts have been favored for autologous transplantation. However, all reports on direct conversion of somatic cells into neural cells have been using transcription factors, which often involve lengthy conversion procedure and are regarded not safe due to integration of viral vector sequence into the genome.

SUMMARY

The present disclosure directs to solve at least one of the problems existing in the prior art. For this purpose, usage of a protein kinase inhibitor in preparing a neural cell from a differentiated non-neural cell, a method for preparing a neural cell, a kit for preparing neural cell, usage of a kit for preparing neural cell, a kind of neural cell or their derivative, and usage of a kind of neural cell or their derivative in preparing drug for the treatment of central nervous system disorder and spinal cord injury are provided.

In one aspect of present disclosure, usage of a protein kinase inhibitor in preparing a neural cell from a differentiated non-neural cell is provided.

According to embodiments of present disclosure, the protein kinase inhibitor is at least one selected from the group consisting of ROCK inhibitor, AKT/mTOR inhibitor, PI3K inhibitor, FAK inhibitor and immunosuppresants.

According to embodiments of present disclosure, the protein kinase inhibitor is at least one selected from the group consisting of ROCK inhibitor, AKT/mTOR inhibitor PI3K inhibitor, FAK inhibitor and immunosuppresants, and preferably the protein kinase inhibitor is at lease selected from the group consisting of Y27632, Palomid 529, LY294002, PF562271 and rapamycin.

According to embodiments of present disclosure, the neural cell is at least one selected from the group consisting of oligodendrocyte progenitor cell, mature oligodendrocyte, neuron and astrocyte.

According to embodiments of present disclosure, the differentiated non-neural cell is at least one selected from the group consisting of human cell, fibroblast cell, epithelial cell, adult cell and neonatal cell.

In a second broad aspect of present disclosure, a method for preparing a neural cell is provided, and according to embodiments of present disclosure, the method may comprise: culturing a differentiated non-neural cell in the present of a protein kinase inhibitor.

According to embodiments of present disclosure, the protein kinase inhibitor is at least one selected from the group consisting of ROCK inhibitor, AKT/mTOR inhibitor, PI3K inhibitor, FAK inhibitor and immunosuppresants.

According to embodiments of present disclosure, the protein kinase inhibitor is at least one selected from the group consisting of ROCK inhibitor, AKT/mTOR inhibitor, PI3K inhibitor, FAK inhibitor and immunosuppresants, and preferably the protein kinase inhibitor is at lease selected from the group consisting of Y27632, Palomid 529, LY294002, PF562271 and rapamycin.

According to embodiments of present disclosure, the neural cell is at least one selected from the group consisting of oligodendrocyte progenitor cell, mature oligodendrocyte, neuron and astrocyte.

According to embodiments of present disclosure, the differentiated non-neural cell is at least one selected from the group consisting of human cell, fibroblast cell, epithelial cell, adult cell and neonatal cell.

In a third broad aspect of present disclosure, a kit is provided, and according to embodiments of present disclosure, the kit may comprise: a first medium, the first medium may comprise: a first basic medium, a protein kinase inhibitor, BDNF, NT3, VPA, dbcAMP, and retinoic acid, wherein the protein kinase inhibitor is at least one selected from the group consisting of ROCK inhibitor, AKT/mTOR inhibitor, PI3K inhibitor, FAK inhibitor and immunosuppresants.

According to embodiments of present disclosure, the kit may further comprises: a second medium, or/and, a third medium, wherein the second medium comprises: a second basic medium, a protein kinase inhibitor, N-2, B-27 without vitamin A, Glutamax, SHH, FGF2, PDGF-AA, and retinoic acid, the third medium comprises: a third basic medium, a protein kinase inhibitor, N-2, B-27 without vitamin A, Glutamax, SHH, Noggin, dbcAMP, IGF, NT3, and retinoic acid, wherein the protein kinase of the second and third medium is independently at least one selected from the group consisting of ROCK inhibitor, AKT/mTOR inhibitor, PI3K inhibitor, FAK inhibitor and immunosuppresants.

According to embodiments of present disclosure, the neural cell is at least one selected from the group consisting of oligodendrocyte progenitor cell, mature oligodendrocyte, neuron and astrocyte.

According to embodiments of present disclosure, the first basic medium is neuronal medium, the second basic medium is DMEM/F12 medium, and the third basic medium is DMEM/F12 medium.

According to embodiments of present disclosure, the protein kinase inhibitor of the second and third medium is independently at least one selected from the group consisting of Y27632, Palomid 529, LY294002, FPF562271 and rapamycin.

According to embodiments of present disclosure, the first medium may comprise: 5 µM-20 µM Y27632, 5 ng/ml-20 ng/ml BDNF, 5 ng/ml-20 ng/ml NT3, 0.5 mM-1.5 mM VPA, 25 µM-100 µM dbcAMP, and 0.5 µM-1 µM retinoic acid; the second medium may comprise: 5 µM-20 µM Y27632, 1×N-2, 1×B-27 without vitamin A, 1× Glutamax, 100 ng/ml-400 ng/ml SHH, 10 ng/ml-40 ng/ml FGF2, 10 ng/ml-40 ng/ml PDGF-AA, and 0.5 µM-1 µM retinoic acid; the third medium may comprise: 5 µM-20 µM Y27632, 1×N-2, 1×B-27 without vitamin A, 1× Glutamax, 100 ng/ml-400 ng/ml SHH, 50 ng/ml-200 ng/ml Noggin, 50 ng/ml-200 ng/ml dbcAMP, 50 ng/ml-200 ng/ml IGF, 5 ng/ml-20 ng/ml NT3, and 0.5 µM-1 µM retinoic acid.

According to embodiments of present disclosure, the first medium may comprise: 10 µM Y27632, 10 ng/ml BDNF, 10 ng/ml NT3, 1 mM VPA, 50 µM dbcAMP, and 0.5 µM retinoic acid; the second medium may comprise: 10 µM Y27632, 1×N-2, 1×B-27 without vitamin A, 1× Glutamax, 200 ng/ml SHH, 20 ng/ml FGF2, 20 ng/ml PDGF-AA, and 0.5 µM retinoic acid; the third medium may comprise: 10 µM Y27632, 1×N-2, 1×B-27 without vitamin A, 1× Glutamax, 200 ng/ml SHH, 100 ng/ml Noggin, 100 ng/ml dbcAMP, 100 ng/ml IGF, 10 ng/ml NT3, and 0.5 µM retinoic acid.

In a fourth broad aspect of present disclosure, usage of the kit for preparing a neural cell is provided.

In a fifth broad aspect of present disclosure, a method for preparing a neural cell is provided, and according to embodiments of present disclosure, the method may comprise:

culturing a differentiated non-neural cell with a first medium, wherein the first medium may comprise: a first basic medium, a protein kinase inhibitor, BDNF, NT3, VPA, dbcAMP, and retinoic acid, wherein the protein kinase inhibitor is at least one selected from the group consisting of ROCK inhibitor, AKT/mTOR inhibitor, PI3K inhibitor, FAK inhibitor and immunosuppresants, wherein the protein kinase inhibitor is at least one selected from the group consisting of Y27632, Palomid 529, LY294002, PF562271 and rapamycin.

According to embodiments of present disclosure, the method for preparing a neural cell further comprises:

Culturing the cell with a second medium or a third medium after the culturing with the first medium.

According to embodiments of present disclosure, the second medium comprises: a second basic medium, a protein kinase inhibitor, N-2, B-27 without vitamin A, Glutamax, SHH, FGF2, PDGF-AA, and retinoic acid, the third medium comprises: a third basic medium, a protein kinase inhibitor, N-2, B-27 without vitamin A, Glutamax, SHH, Noggin, dbcAMP, IGF, NT3, and retinoic acid, according to embodiments of present disclosure, the protein kinase inhibitor of the second and the third medium is independently at least one selected from the group consisting of ROCK inhibitor, AKT/mTOR inhibitor, PI3K inhibitor, FAK inhibitor and immunosuppresants.

According to embodiments of present disclosure, the neural cell is at least one selected from the group consisting of oligodendrocyte progenitor cell, mature oligodendrocyte, neuron and astrocyte.

According to embodiments of present disclosure, the differentiated non-neural cell is at least one selected from the group consisting of human cell, fibroblast cell, epithelial cell, adult cell and neonatal cell.

According to embodiments of present disclosure, the first basic medium is neuronal medium, the second basic medium is DMEM/F12 medium, the third basic medium is DMEM/F12 medium.

According to embodiments of present disclosure, the protein kinase inhibitor of the second and the third medium is independently at least one selected from the group consisting of Y27632, Palomid 529, LY294002, PF562271 and rapamycin.

According to embodiments of present disclosure, the first medium may comprise: 5 µM-20 µM Y27632, 5 ng/ml-20 ng/ml BDNF, 5 ng/ml-20 ng/ml NT3, 0.5 mM-1.5 mM VPA, 25 µM-100 µM dbcAMP, and 0.504-1 µM retinoic acid; the second medium may comprise: 50 µM-2004 Y27632, 1×N-2, 1×B-27 without vitamin A, 1× Glutamax, 100 ng/ml-400 ng/ml SHH, 10 ng/ml-40 ng/ml FGF2, 10 ng/ml-40 ng/ml PDGF-AA, and 0.5 µM-1 µM retinoic acid; the third medium may comprise: 50 µM-20 µM Y27632, 1×N-2, 1×B-27 without vitamin A, 1× Glutamax, 100 ng/ml-400 ng/ml SHH, 50 ng/ml-200 ng/ml Noggin, 50 ng/ml-200 ng/ml dbcAMP, 50 ng/ml-200 ng/ml IGF, 5 ng/ml-20 ng/ml NT3, and 0.5 µM-1 µM retinoic acid.

According to embodiments of present disclosure, the first medium may comprise: 10 µM Y27632, 10 ng/ml BDNF, 10 ng/ml NT3, 1 mM VPA, 50 µM dbcAMP, and 0.5 µM retinoic acid; the second medium may comprise: 1004 Y27632, 1×N-2, 1×B-27 without vitamin A, 1× Glutamax, 200 ng/ml SHH, 20 ng/ml FGF2, 20 ng/ml PDGF-AA, and 0.504 retinoic acid; the third medium may comprise: 1004 Y27632, 1×N-2, 1×B-27 without vitamin A, 1× Glutamax, 200 ng/ml SHH, 100 ng/ml Noggin, 100 ng/ml dbcAMP, 100 ng/ml IGF, 10 ng/ml NT3, and 0.504 retinoic acid.

In a sixth broad aspect of present disclosure, a neural cell or their derivative is provided, and according to embodiments of present disclosure, the neural cell or their derivative is obtainable by the method for preparing a neural cell.

In a seventh broad aspect of present disclosure, usage of the neural cell or their derivative in preparing a drug for the treatment of central nervous system disorder and spinal cord injury is provided.

According to embodiments of present disclosure, the Central nervous system disorder is at least one selected from the group consisting of Alzheimer's Disease, Parkinsin's Disease, Amyotrophic Lateral Sclerosis, Multiple Sclerosis, and Leukodystrophies.

The above summary of the present disclosure is not intended to describe each disclosed embodiment or every implementation of the present disclosure. The Figures and the detailed description which follow more particularly exemplify illustrative embodiments.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference the accompanying drawings, in which.

Figure 2:
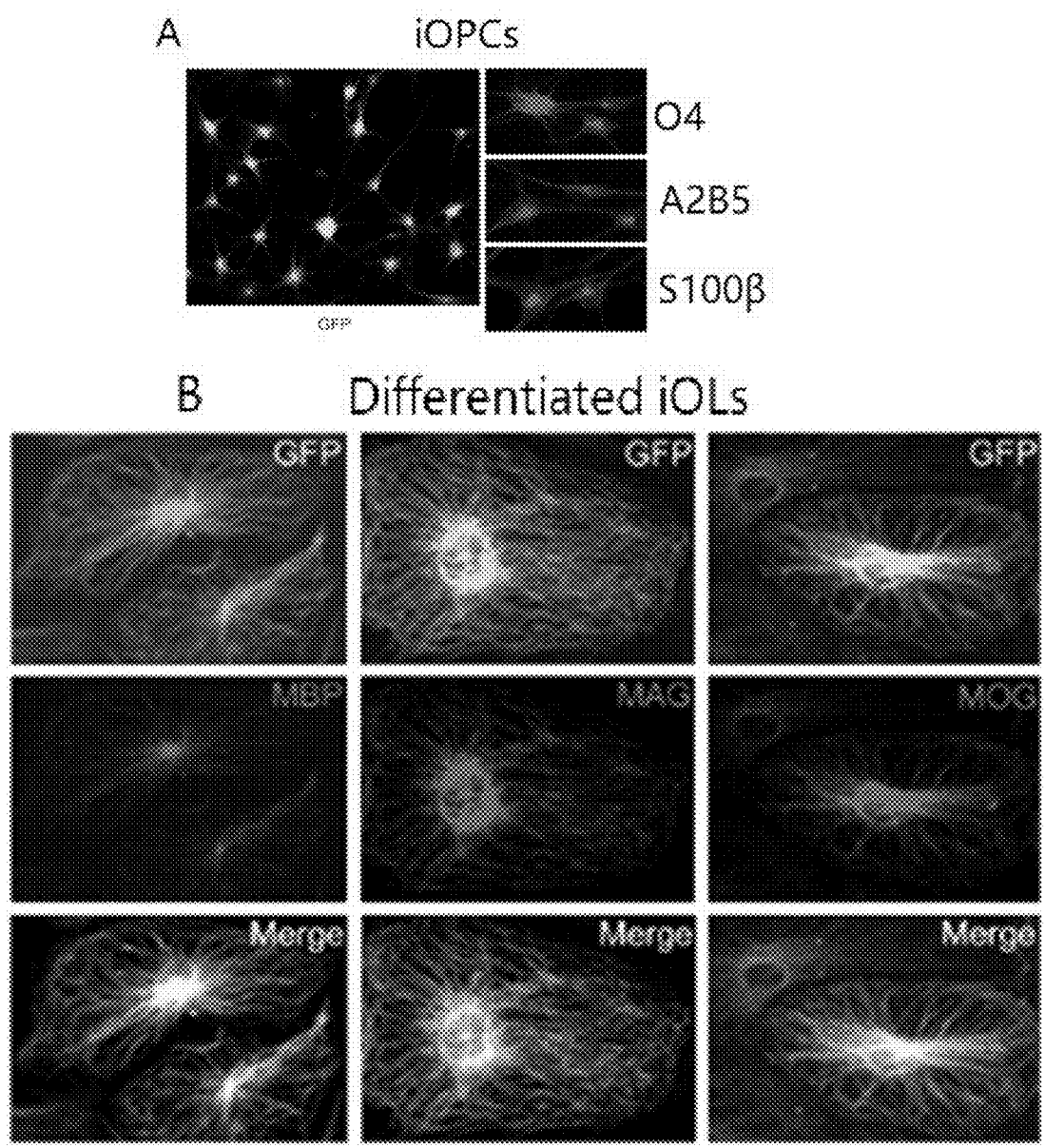
Figure 3:
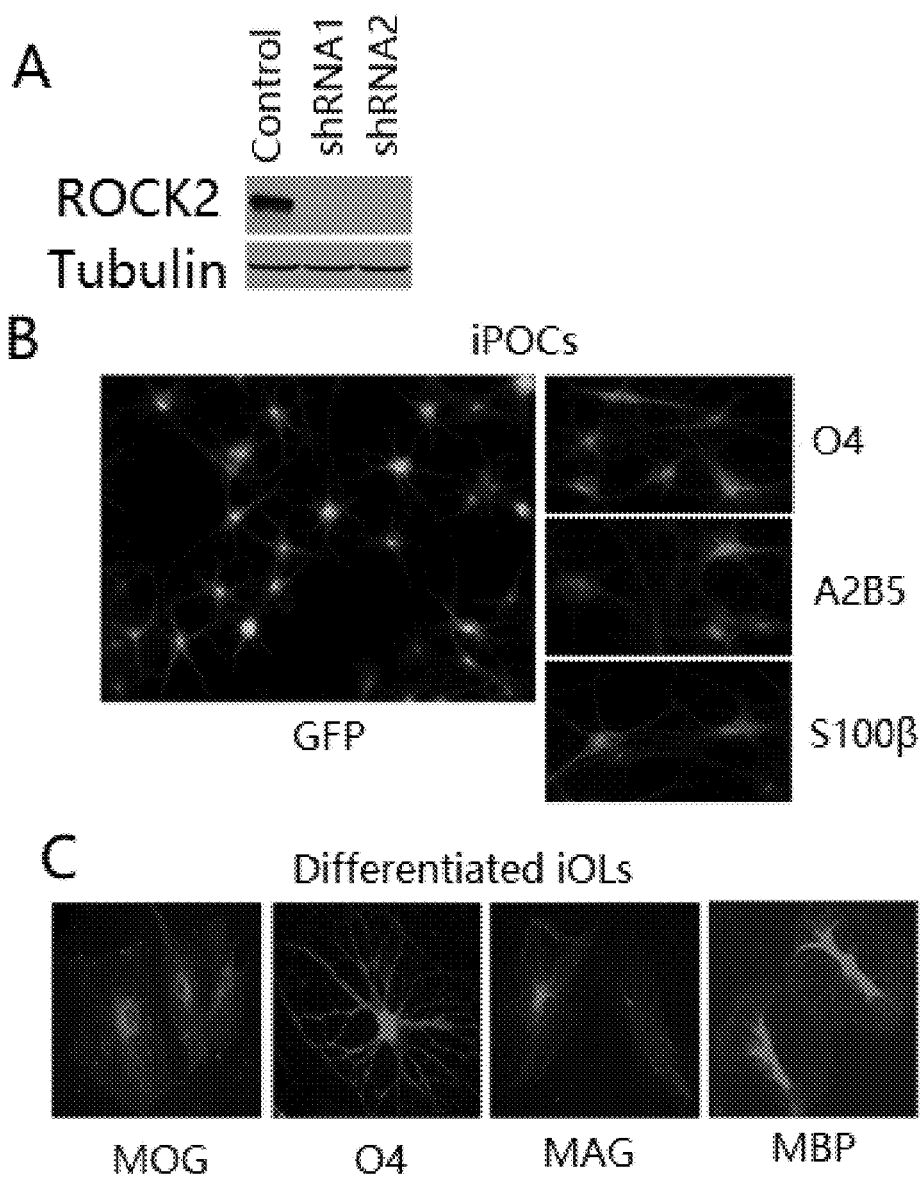
Figure 4:
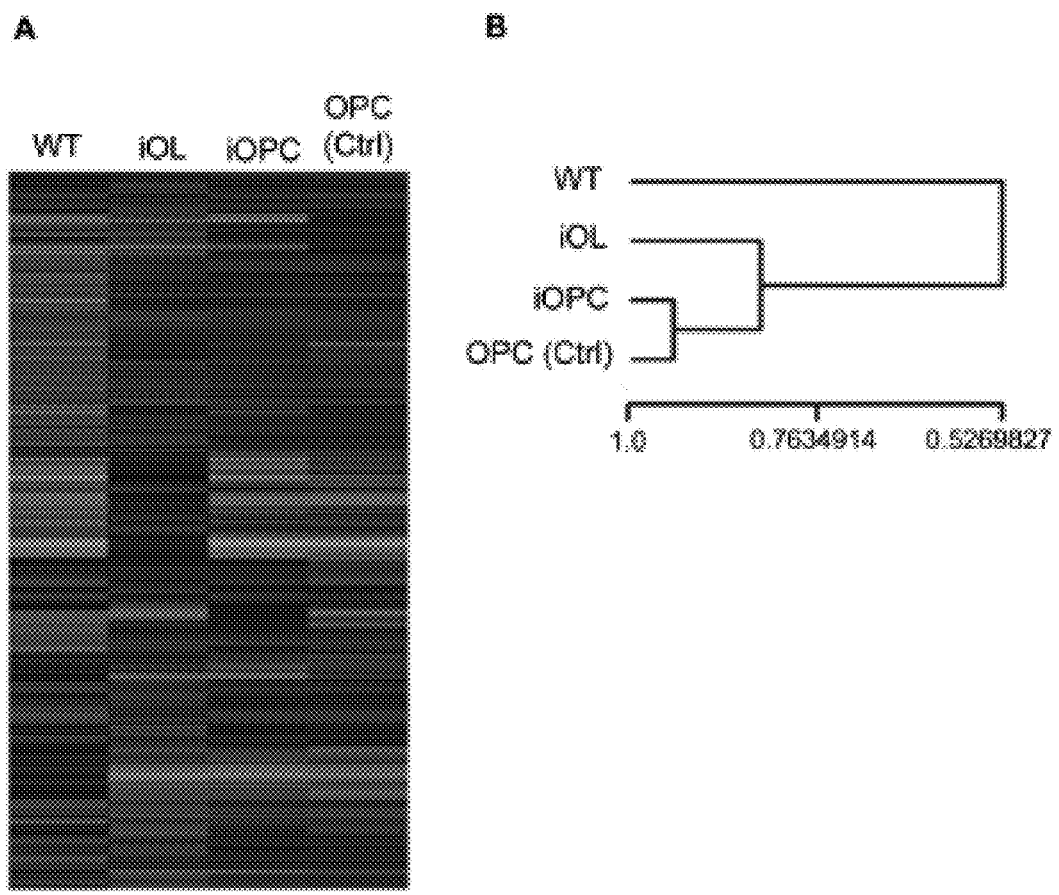
Figure 5:
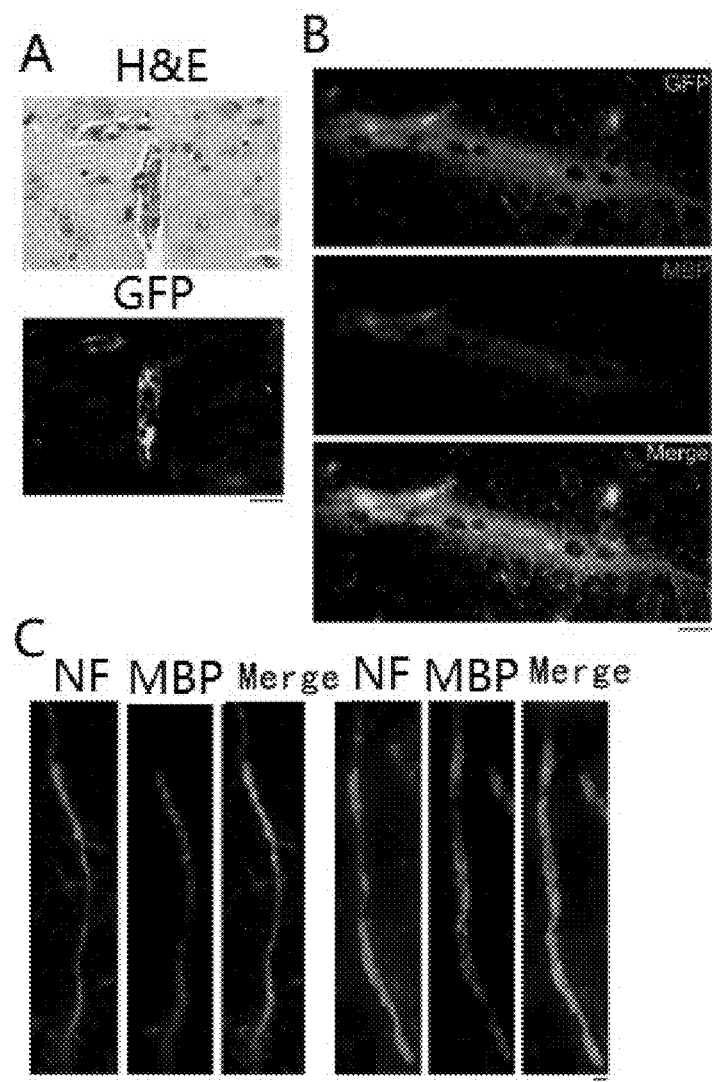
Figure 6:
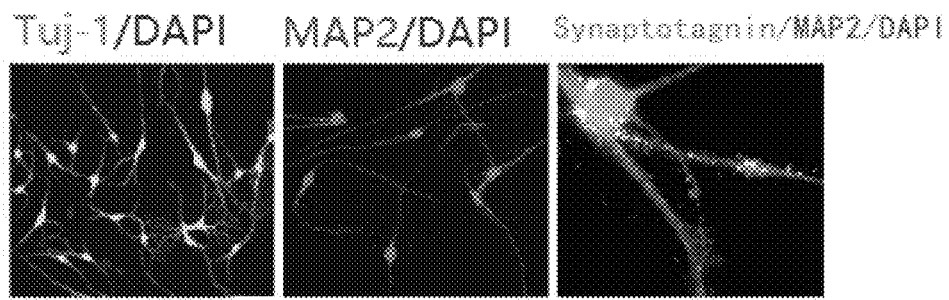
Figure 7:
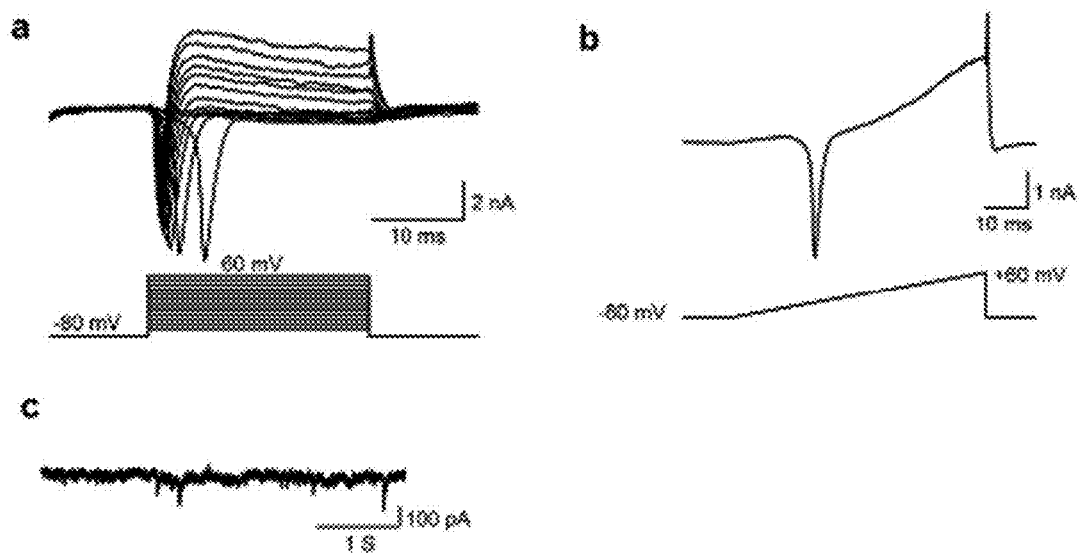
Figure 8:
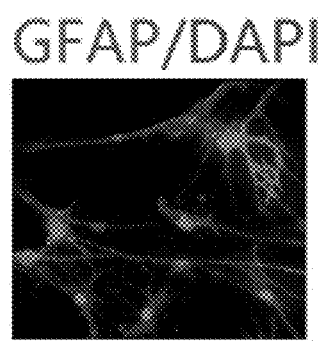

a. Design of the screening of protein kinase inhibitor library, b. Representative hits of kinase inhibitor. Essential hits were identified by OPC morphology. Images were taken on day 7 post inhibitor treatment, c. OPC positive cells were counted by morphology and quantified on day 7;

FIG. 2 is a graph showing the immunostaining result of iOPCs and iOLs (induced oligodendrocytes) according to an embodiment of the present disclosure.

a. GFP-positive iOPCs with bi- or multiple neurites processing out of the cell body from Y27632-treated adult dermal fibroblasts 7 days after induction. The images of the right panel showed the induced O4, A2B5 and S100β-positive OPCs, b. iOPCs were cultured in the third medium to differentiate into iOLs. The images showed the MBP, MAG and MOG-positive OPCs;

FIG. 3 is a graph showing the result of immunostaining and Western blot according to an embodiment of the present disclosure, a. Western blot analysis showed that ROCK2 shRNA1 and shRNA2 are sufficient to inhibit ROCK2 expression in adult dermal fibroblasts, b. Adult dermal fibroblasts were transduced with ROCK2 shRNA1 and then cultured in induction medium for 7 days. The images showed GFP, O4, A2B5 and S100β-positive OPCs, c. iOPCs with expressing ROCK2 shRNA1 were cultured in the third medium to differentiate into iOLs. The images showed the MBP, MAG and MOG-positive OPCs;

FIG. 4 is a graph showing the Global gene expression profiling of iOPCs and iOLs according to an embodiment of the present disclosure, a. Heat-map of genes differentially expressed in global RNA-microarray analysis performed on adult dermal fibroblasts (WT), ROCK inhibitor-iOLs, iOPCs and brain-derived positive control OPCs, b. Hierarchical clustering;

FIG. 5 is a graph showing the result of immuno-histochemical detection according to an embodiment of the present disclosure, a. ROCK inhibitor-iOPCs were injected into cuprizone-treated mice and brains were analyzed 4 weeks later. Representative immnofluorenscent image and matched section stained with H&E, b. GFP/MBP-positive cells were detected in all iOPC injection sites analyzed (n=6). Nuclei were counterstained with DAPI (blue), c. Confocal projection images showed that the MBP+ tube-like structures associate with neurofilament (NF) to wrap nerve fibers, Scale bar, 20 μm (a); 5 μm (b, c);

FIG. 6 is a graph showing the immunostaining result of IMR90 fibroblasts treated by a combination of ROCK and AKT/mTOR inhibitors according to an embodiment of the present disclosure, showing neuron specific markers Tuj1, MAP2, and Synaptotagmin;

FIG. 7 is a graph showing the electrophysiological characterization of induced neurons according to an embodiment of the present disclosure, a. Representative current traces (upper panel) recorded in voltage-clamp mode. Cells were depolarized by voltage steps from −60 to +60 mV in 10-mV increments (Δ10 mV, upper panel). The lower panel shows the current-voltage (I-V) relationship for sodium current, b. Representative traces of membrane currents recorded with a ramp protocol (lower panel, a voltage ramp from −80 mV to +60 mV over 500 ms). Fast activating Na+ current were prominent, c. Sample traces of spontaneous synaptic currents (without pharmacological blockers) recorded at a holding potential of −80 mV;

FIG. 8 is a graph showing the immunostaining result of IMR90 fibroblasts 1 weeks after treated by a combination of ROCK and mTOR inhibitors (n=3) according to an embodiment of the present disclosure, showing astrocyte specific marker GFAP.

DETAILED DESCRIPTION

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

In one aspect of present disclosure, usage of a protein kinase inhibitor in preparing a neural cell from a differentiated non-neural cell is provided. Inventors found that, the protein kinase inhibitor is able to convert the differentiated non-neural cell into the neural cell efficiently, without using any transcription factor.

According to embodiments of present disclosure, the protein kinase inhibitor is at least one selected from the group consisting of ROCK inhibitor, AKT/mTOR inhibitor, PI3K inhibitor, FAK inhibitor and immunosuppresants. Using the protein kinase inhibitor can convert the differentiated non-neural cell into the neural cell efficiently.

According to embodiments of present disclosure, the protein kinase inhibitor is at least one selected from the group consisting of ROCK inhibitor, AKT/mTOR inhibitor PI3K inhibitor, FAK inhibitor and immunosuppresants, and preferably the protein kinase inhibitor is at lease selected from the group consisting of Y27632, Palomid 529, LY294002, PF562271 and rapamycin. The protein kinase inhibitor is sufficient to reprogram the differentiated non-neural cell into the neural cell.

According to embodiments of present disclosure, the neural cell is at least one selected from the group consisting of oligodendrocyte progenitor cell, mature oligodendrocyte, neuron and astrocyte. The neural cell is suitable for treatment of central nervous system disorder and spinal cord injury with a much lower risk of cancer and treatoma formation.

According to embodiments of present disclosure, the differentiated non-neural cell is at least one selected from the group consisting of human cell, fibroblast cell, epithelial cell, adult cell and neonatal cell. Thus, the differentiated non-neural cell can convert into the neural cell efficiently in the present of the protein kinase inhibitor.

In a second broad aspect of present disclosure, a method for preparing a neural cell is provided, and according to embodiments of present disclosure, the method may comprise: culturing a differentiated non-neural cell in the present of a protein kinase inhibitor. The method of present disclosure provides a novel and safe procedure for making large quantities of neural cells for autologous cell transplantation to treat central nervous system (CNS) disorder, particularly, diseases associated with demyelination.

According to embodiments of present disclosure, the protein kinase inhibitor is at least one selected from the group consisting of ROCK inhibitor, AKT/mTOR inhibitor, PI3K inhibitor, FAK inhibitor and immunosuppresants. Using the protein kinase inhibitor can convert the differentiated non-neural cell into the neural cell efficiently.

According to embodiments of present disclosure, the protein kinase inhibitor is at least one selected from the group consisting of ROCK inhibitor, AKT/mTOR inhibitor, PI3K inhibitor, FAK inhibitor and immunosuppresants, and preferably the protein kinase inhibitor is at lease selected from the group consisting of Y27632, Palomid 529, LY294002, PF562271 and rapamycin. The protein kinase inhibitor is sufficient to reprogram the differentiated non-neural cell into the neural cell.

According to embodiments of present disclosure, the neural cell is at least one selected from the group consisting of oligodendrocyte progenitor cell, mature oligodendrocyte, neuron and astrocyte. The neural cell is suitable for treatment of central nervous system disorders and spinal cord injury with a much lower risk of cancer and teratoma formation.

According to embodiments of present disclosure, the differentiated non-neural cell is at least one selected from the group consisting of human cell, fibroblast cell, epithelial cell, adult cell and neonatal cell. Thus, the differentiated non-neural cell can convert into the neural cell efficiently in the present of the protein kinase inhibitor.

In a third broad aspect of present disclosure, a kit is provided, and according to embodiments of present disclosure, the kit may comprise: a first medium, the first medium may comprise: a first basic medium, a protein kinase inhibitor, BDNF, NT3, VPA, dbcAMP, and retinoic acid, according to embodiments of present disclosure, the protein kinase inhibitor is at least one selected from the group consisting of ROCK inhibitor, AKT/mTOR inhibitor, PI3K inhibitor, FAK inhibitor and immunosuppresants. Using the kit of present disclosure, the differentiated non-neural cell can be induced into the neural cell directly. The induced neural cells expressed typical biomarkers of their specific cell types.

According to embodiments of present disclosure, the kit may future comprises: a second medium, or/and, a third medium, according to embodiments of present disclosure, the second medium comprises: a second basic medium, a protein kinase inhibitor, N-2, B-27 without vitamin A, Glutamax, SHH, FGF2, PDGF-AA, and retinoic acid, the third medium comprises: a third basic medium, a protein kinase inhibitor, N-2, B-27 without vitamin A, Glutamax, SHH, Noggin, dbcAMP, IGF, NT3, and retinoic acid, according to embodiments of present disclosure, the protein kinase inhibitor of the second and third medium is independently at least one selected from the group consisting of ROCK inhibitor, AKT/mTOR inhibitor, PI3K inhibitor, FAK inhibitor and immunosuppresants. Using the second medium or the third medium, the differentiated non-neural cell can convert into functional neuron or astrocyte.

According to embodiments of present disclosure, the neural cell is at least one selected from the group consisting of oligodendrocyte progenitor cell, mature oligodendrocyte, neuron and astrocyte. The neural cell is suitable for treatment of central nervous system disorder and spinal cord injury with a much lower risk of cancer and teratoma formation.

According to embodiments of present disclosure, the first basic medium is neuronal medium, the second basic medium is DMEM/F12 medium, the third basic medium is DMEM/F12 medium. The basic mediums mentioned above are in favor of the conversion from the differentiated non-neural cell to the neural cell.

According to embodiments of present disclosure, the protein kinase inhibitor of the second and third medium is independently at least one selected from the group consisting of Y27632, Palomid 529, LY294002, PF562271 and rapamycin. The protein kinase inhibitor is sufficient to reprogram the differentiated non-neural cell into the neural cell.

According to embodiments of present disclosure, the first medium may comprise: 5 µM-20 µM Y27632, 5 ng/ml-20 ng/ml BDNF, 5 ng/ml-20 ng/ml NT3, 0.5 mM-1.5 mM VPA, 25 µM-100 µM dbcAMP, and 0.5 µM-1 µM retinoic acid; the second medium may comprise: 5 µM-20 µM Y27632, 1×N-2, 1×B-27 without vitamin A, 1× Glutamax, 100 ng/ml-400 ng/ml SHH, 10 ng/ml-40 ng/ml FGF2, 10 ng/ml-40 ng/ml PDGF-AA, and 0.5 µM-1 µM retinoic acid; the third medium may comprise: 5 µM-20 µM Y27632, 1×N-2, 1×B-27 without vitamin A, 1× Glutamax, 100 ng/ml-400 ng/ml SHH, 50 ng/ml-200 ng/ml Noggin, 50 ng/ml-200 ng/ml dbcAMP, 50 ng/ml-200 ng/ml IGF, 5 ng/ml-20 ng/ml NT3, and 0.5 µM-1 µM retinoic acid. Thus, the differentiated non-neural cell will convert into the neural cell quickly and efficiently when cultured with the medium mentioned above, and the conversion rate is very high.

According to embodiments of present disclosure, the first medium may comprise: 10 µM Y27632, 10 ng/ml BDNF, 10 ng/ml NT3, 1 mM VPA, 50 µM dbcAMP, and 0.5 µM retinoic acid; the second medium may comprise: 10 µM Y27632, 1×N-2, 1×B-27 without vitamin A, 1× Glutamax, 200 ng/ml SHH, 20 ng/ml FGF2, 20 ng/ml PDGF-AA, and 0.5 µM retinoic acid; the third medium may comprise: 10 µM Y27632, 1×N-2, 1×B-27 without vitamin A, 1× Glutamax, 200 ng/ml SHH, 100 ng/ml Noggin, 100 ng/ml dbcAMP, 100 ng/ml IGF, 10 ng/ml NT3, and 0.5 µM retinoic acid. Thus, the differentiated non-neural cell will convert into the neural cell quickly and efficiently when cultured with the medium mentioned above, and the conversion rate is very high. Besides, the neural cell is suitable for autologous transplantation to treat central nervous system disorder and spinal cord injury with a much lower risk of cancer and teratoma formation, and there is no immune rejection.

In a fourth broad aspect of present disclosure, usage of the kit for preparing a neural cell is provided. Using the kit of present disclosure, large quantities of neural cells can be obtained, and the neural cell is suitable for autologous transplantation to treat central nervous system disorder and spinal cord injury with a much lower risk of cancer and teratoma formation, and there is no immune rejection.

In a fifth broad aspect of present disclosure, a method for preparing a neural cell is provided, and according to embodiments of present disclosure, the method may comprise:

Culturing a differentiated non-neural cell with a first medium,

According to embodiments of present disclosure, the first medium may comprise: a first basic medium, a protein kinase inhibitor, BDNF, NT3, VPA, dbcAMP, and retinoic acid, according to embodiments of present disclosure, the protein kinase inhibitor is at least one selected from the group consisting of ROCK inhibitor, AKT/mTOR inhibitor, PI3K inhibitor, FAK inhibitor and immunosuppresants, according to embodiments of present disclosure, the protein kinase inhibitor is at least one selected from the group consisting of Y27632, Palomid 529, LY294002, PF562271 and rapamycin. Using the first medium can directly convert the differentiated non-neural cell into the neural cell.

According to embodiments of present disclosure, the method for preparing a neural cell further comprises:

Culturing the cell with a second medium or a third medium after the culturing with the first medium.

According to embodiments of present disclosure, the second medium comprises: a second basic medium, a protein kinase inhibitor, N-2, B-27 without vitamin A, Glutamax, SHH, FGF2, PDGF-AA, and retinoic acid, the third medium comprises: a third basic medium, a protein kinase inhibitor, N-2, B-27 without vitamin A, Glutamax, SHH, Noggin, dbcAMP, IGF, NT3, and retinoic acid, according to embodiments of present disclosure, the protein kinase inhibitor of the second and the third medium is independently at least one selected from the group consisting of ROCK inhibitor, AKT/mTOR inhibitor, PI3K inhibitor, FAK inhibitor and immunosuppresants. Using the second medium or the third medium, the differentiated non-neural cell can convert into functional neuron or astrocyte.

According to embodiments of present disclosure, the neural cell is at least one selected from the group consisting of oligodendrocyte progenitor cell, mature oligodendrocyte, neuron and astrocyte. The neural cell is suitable for treatment of central nervous system disorder and spinal cord injury with a much lower risk of cancer and teratoma formation, and there is no immune injection.

According to embodiments of present disclosure, the differentiated non-neural cell is at least one selected from the group consisting of human cell, fibroblast cell, epithelial cell, adult cell and neonatal cell. Thus, the differentiated non-neural cell can convert into the neural cell efficiently in the present of the protein kinase inhibitor.

According to embodiments of present disclosure, the first basic medium is neuronal medium, the second basic medium is DMEM/F12 medium, and the third basic medium is DMEM/F12 medium. The basic mediums mentioned above are in favor of the conversion from the differentiated non-neural cell to the neural cell.

According to embodiments of present disclosure, the protein kinase inhibitor of the second and the third medium is independently at least one selected from the group consisting of Y27632, Palomid 529, LY294002, PF562271 and rapamycin. The protein kinase inhibitor is sufficient to reprogram the differentiated non-neural cell into the neural cell.

According to embodiments of present disclosure, the first medium may comprise: 5 μM-20 μM ROCK inhibitor (Y27632), 5 ng/ml-20 ng/ml BDNF, 5 ng/ml-20 ng/ml NT3, 0.5 mM-1.5 mM VPA, 25 μM-100 μM dbcAMP, and 0.5 μM-1 μM retinoic acid; the second medium may comprise: 5 μM-20 μM ROCK inhibitor (Y27632), 1×N-2, 1×B-27 without vitamin A, 1× Glutamax, 100 ng/ml-400 ng/ml SHH, 10 ng/ml-40 ng/ml FGF2, 10 ng/ml-40 ng/ml PDGF-AA, and 0.5 μM-1 μM retinoic acid; the third medium may comprise: 5 μM-20 μM ROCK inhibitor (Y27632), 1×N-2, 1×B-27 without vitamin A, 1× Glutamax, 100 ng/ml-400 ng/ml SHH, 50 ng/ml-200 ng/ml Noggin, 50 ng/ml-200 ng/ml dbcAMP, 50 ng/ml-200 ng/ml IGF, 5 ng/ml-20 ng/ml NT3, and 0.5 μM-1 μM retinoic acid. Thus, the differentiated non-neural cell will convert into the neural cell quickly and efficiently when cultured with the medium mentioned above, and the conversion rate is very high.

According to embodiments of present disclosure, the first medium may comprise: 10 μM Y27632, 10 ng/ml BDNF, 10 ng/ml NT3, 1 mM VPA, 50 μM dbcAMP, and 0.5 μM retinoic acid; the second medium may comprise: 10 μM Y27632, 1×N-2, 1×B-27 without vitamin A, 1× Glutamax, 200 ng/ml SHH, 20 ng/ml FGF2, 20 ng/ml PDGF-AA, and 0.5 μM retinoic acid; the third medium may comprise: 10 μM Y27632, 1×N-2, 1×B-27 without vitamin A, 1× Glutamax, 200 ng/ml SHH, 100 ng/ml Noggin, 100 ng/ml dbcAMP, 100 ng/ml IGF, 10 ng/ml NT3, and 0.5 μM retinoic acid. Thus, the differentiated non-neural cell will convert into the neural cell quickly and efficiently when cultured with the medium mentioned above, and the conversion rate is very high. Besides, the neural cell is suitable for autologous transplantation to treat central nervous system disorder and spinal cord injury with a much lower risk of cancer and teratoma formation, and there is no immune rejection.

In a sixth broad aspect of present disclosure, a neural cell or their derivative is provided, and according to embodiments of present disclosure, the neural cell or their derivative obtainable by the method for preparing a neural cell. The neural cell or its derivative is suitable for the treatment of central nervous system disorder and spinal cord injury.

In a seventh broad aspect of present disclosure, usage of the neural cell or their derivative in preparing a drug for the treatment of central nervous system disorder and spinal cord injury is provided.

According to embodiments of present disclosure, the central nervous system disorder is at least one selected from the group consisting of Alzheimer's Disease, Parkinsin's Disease, Amyotrophic Lateral Sclerosis, Multiple Sclerosis, and Leukodystrophies.

Example 1: Screening of Protein Kinase Inhibitor Library

1. Coated cell culture 24-well plate with 0.1 mg/ml Poly-L-ornithine solution (sigma, P4957) for at least 3 hours. Then washed wells 3 times with autoclaved MilliQ water, 5 mins per time.

2. Added 500 ul/well of 2 pg/ml Fibronectin (sigma, F0556) and 10 pg/ml Laminin (ROCHE, 11243217001) solution in 1×PBS and placed in incubator overnight to coat.

3. Aspirated the Fibronectin/Laminin solution from the wells, washed with culture medium.

4. Plated fibroblast cells with Basic Medium at $2 \times 10^{\wedge}4$ cells (human adult dermal fibroblasts, ATCC, PCS-201-012) per well, cultured overnight. The Basic Medium comprises: DMEM high glucose (HyClone, SH30022), 10% FBS (Fisher Scientific, SH3007003), 10 mM HEPES (CORNING 25060-CL), 1×MEM NEAA (100×) (GIBCO, 11140) (MEM Non-Essential Amino Acids Solution), 1 mM Na Pyruvate (GIBCO, 25000), 1×2-Mercaptoethanol (1000×) (GIBCO, 21985), 1× Glutamax (100×) (GIBCO, 35050), penicillin/streptomycin.

5. Aspirated Basic Medium from the wells.
6. Washed with PBS once.
7. Fed wells with Induction Medium. Changed medium every two days. The Induction Medium comprises: Neuronal Medium (ScienCell, 1521), 10 ng/ml BDNF (PROSPEC, CYT-207) (Brain-Derived Neurotrophic Factor), 10 ng/ml NT3 (PROSPEC, CYT-257) (neurotrophin 3), 1 mM VPA (sigma, P4543) (Valproic acid sodium salt), 50 µM dbcAMP (sigma, D0627) (Dibutyryl cAMP sodium salt), penicillin/streptomycin, 0.5 µM RA (Retinoic acid) (sigma, R2625), 2 µM protein inhibitor (protein kinase inhibitor library, Library I, II, III: 240 inhibitors, Calbiochem, Cat#539744, 539745 & 539746).
8. When cells changed their morphology into neural-like cells (about 7 days from fibroblasts seeding), cultured cells with Mature Medium or OPC medium (DMEM/F12, Invitrogen, 11320), 1×N-2 (R&D Systems), 1×B-27 without vitamin A (Invitrogen), 1× Glutamax (GIBCO, 35050), 200 ng/ml SHH (R&D Systems), 20 ng/ml FGF2 (R&D Systems), 20 ng/ml PDGF-AA (R&D Systems), secondary antibody, 10 µM Y-27632 (Enzo Life Sciences, ALX-270-333-M005), 0.5 µM RA (Sigma, R2625) for induction of OPCs.

Inventors found that addition of kinase inhibitors can generate neural cells from human adult dermal fibroblasts with high efficiency in defined neural induction media, whereas no conversion was observed without kinase inhibitor. In particular, inventors observed that a subpopulation of fibroblasts underwent a marked morphological change in only 3-7 days in neural induction medium with kinase inhibitor treatments, from large, flat, spindle shaped cells (fibroblasts) to small, bi- of multi-polar cells, termed iOPCs (FIG. 1b). After the initial screening, inventors selected the top 5 candidate inhibitors that efficiently induced fibroblast—OPC conversion for further analysis (FIG. 1c) and found that using a ROCK inhibitor (Y27632) with retinoic acid (RA) converted human fibroblasts into iOPCs with the highest efficiency (~80%, FIG. 1c).

Example 2

Figure 1:
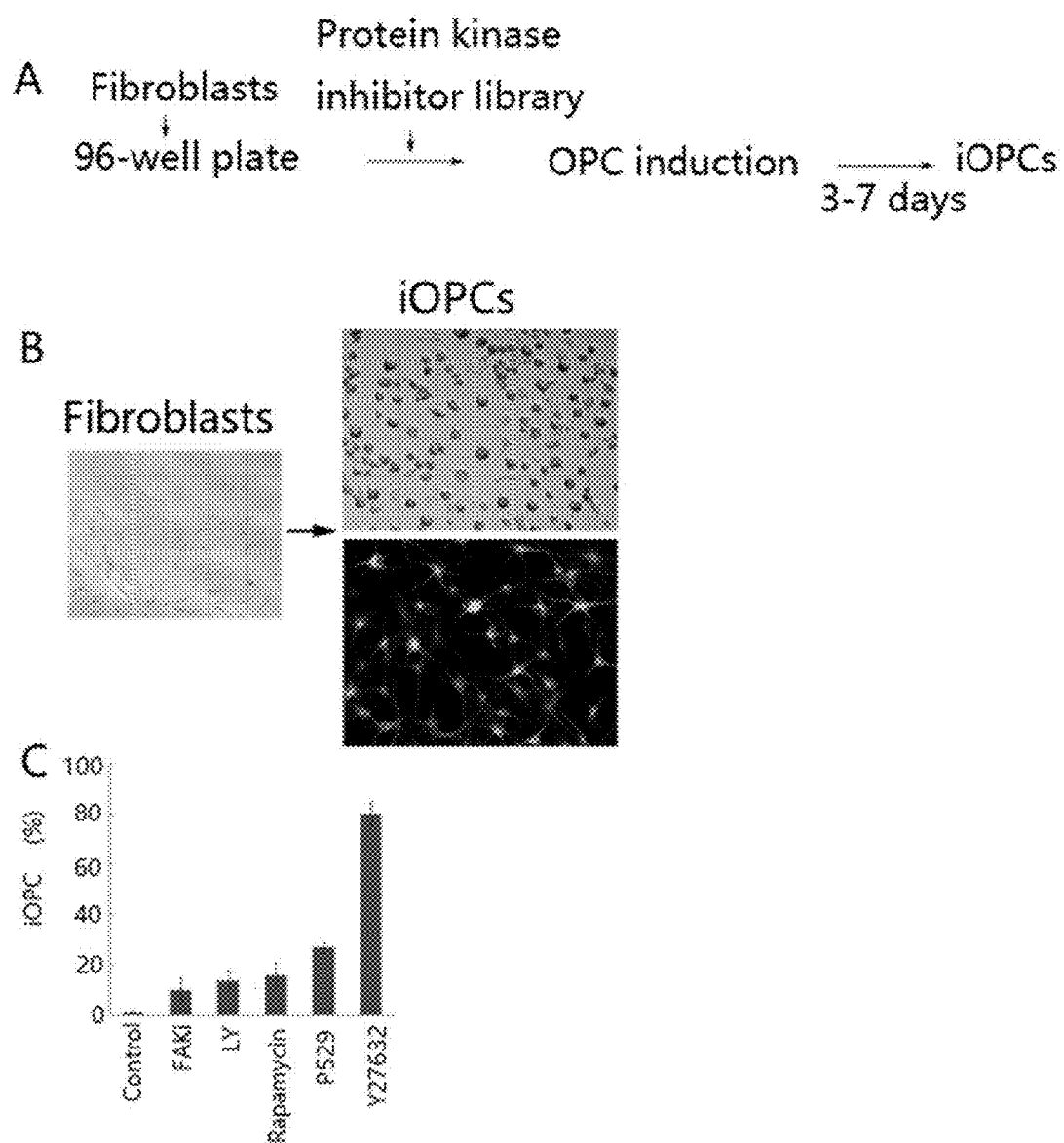
FIG. 1 is a graph showing the immunostaining result of iOPCs (induced oligodendrocyte progenitor cells) according to an embodiment of the present disclosure.

Using the same method with EXAMPLE 1, cultured fiber cell line IMR90 and WI38 with neural induction medium including 10 µM Y27632, Palomid 529, LY294002, PF562271 or rapamycin. The result showed that: cultured for a period of time with neural induction medium including the protein kinase inhibitor, both of the fiber cell line IMR90 and WI38 converted into neural cell, FIG. 1 showed the picture of the induced neural cells.

Example 3

After 7-day induction with ROCK inhibitor treatment, cells were fixed and analyzed by immunostaining of the OPC-specific biomarker, O4. Immunofluorescence staining was performed as following steps:

Briefly, 5×10⁴ modified human fibroblasts were planted on coated glass coverslips the day before induction. After induction, cells were fixed for 20 min at room temperature in 4% paraformaldehyde in PBS, permeabilized for 30 min in PBS containing 0.2% Triton X-100 and 10% normal goat serum (NGS), and incubated overnight at 4° C. in PBS containing 10% NGS and primary antibodies. Then cells were washed three times with PBS and incubated for 2 h at room temperature with anti-rabbit or anti-mouse secondary antibodies Alexa Fluor-488 or Alexa Fluor-594 (1:500, Invitrogen). The images were acquired by immunofluorescence microscope or Zeiss LSM 510 META confocal microscope with 40×, 1.3 numerical aperture oil-immersion objective.

The following antibodies were used for the immunofluorescence studies: mouse anti-O4 (Millipore, 1:50), rabbit anti-NF (Sigma-Aldrich, 1:1000), mouse anti-A2B5 (Millipore, 1:50), MBP (1:100, Covance; 1:100, Abcam), MAG (Millipore, 1:50), MOG (Millipore, 1:50).

The result showed that about 80% of dermal fibroblasts were converted to O4-positive cells with characteristic morphology of oligodendrocyte progenitor cells (OPC) (FIG. 2a). Furthermore, these O4 positive cells also showed positive staining with two additional OPC markers, A2B5 and S100β (FIG. 2a). In contrast, after 4 weeks in the same induction medium without ROCK inhibitor, cells kept fibroblast morphology with negative staining of O4, A2B5, and S100β (data not shown). These results suggest that ROCK inhibitor leads to direct conversion of human fibroblasts to iOPCs. To confirm conversion of fibroblasts to iOPCs by ROCK inhibitor, additional two human primary fibroblast cell lines, IMR90 and WI38, were tested using the same fibroblast—OPC conversion conditions. Consistent with the results from adult dermal cells, inventors observed 60-80% of fibroblast—OPC conversion in these two cell lines (data not shown). Next, inventors assessed whether the iOPCs could differentiate into mature oligodendrocytes. After removing growth factors and addition of thyroid hormone (a known inducer of oligodendrocyte differentiation) in cell culture medium, about 70% of the iOPCs differentiated into cells with a multiprocessed morphology typical of oligodendrocytes within 3-7 days (FIG. 2b). The oligodendrocytes expressed myelin basic protein (MBP), an integral protein component of the myelin sheath, and other defining markers of mature oligodendrocytes, including myelin-associated glycoprotein and myelin oligodendrocyte glycoprotein (FIG. 2b). Thus, inventors concluded that ROCK inhibitor-induced iOPCs can be further differentiated into mature functional oligodendrocytes.

Example 4

ROCK is a kinase belonging to the AGC (PKA/PKG/PKC) family of serine-threonine kinases, including ROCK1 and ROCK2 in mammals (human, rat, mouse). ROCK1 is mainly expressed in the lung, liver, spleen, kidney and testis, while ROCK2 is distributed mostly in the brain and heart. To determine if the Rho-ROCK pathway is involved in fibroblast-OPC conversion, inventors examined the effects of ROCK knockdown on fibroblast-OPC conversion. Lentiviral constructs expressing short hairpin RNAs (Sigma-Aldrich, TRCN0000342532, TRCN0000342473) against ROCK2 gene were transfected to human adult dermal fibroblasts. Transfected cells showed significantly reduced ROCK2 expression (FIG. 3a) and gave a fibroblast-OPC conversion rate (60-80%) similar to that of ROCK inhibitor treatment. The iOPCs induced by ROCK2 knockdown showed positive staining for OPC markers O4, A2B5 and S100β (FIG. 3b). Moreover, these iOPCs differentiated into cells with typical oligodendrocytes morphology with positive staining of OL markers MBP, MAC, and MOG (FIG. 3c). This result further confirmed that ROCK2 kinase is involved in conversion of fibroblast to neural cells.

Example 5

Inventors hypothesize that ROCK inhibitor induces fibroblast-OPC conversion by regulating a set of neural transcription factors. To analyze the similarities among iOPCs, human brain-derived OPCs, iOLs and parental fibroblasts, inventors generated comparative global gene expression data by microarray analysis.

Microarray analysis was performed at the Washington University Genome Center. Briefly, Illumina HumanHT-12 v4 Expression BeadChip was used and samples were labeled by biotin. The Direct Hybridization Assay was performed and the data were scanned on the BeadArray Reader. Scanned images were quantitated by Illumina Beadscan, v3. Quantitative data was imported into Illumina GenomeStudio software and normalized by Illumina's quantile method. The quantile-normalized background-subtracted data were calculated in excel. The data were filtered based on the average signal, and set the baseline as 50 so that only the genes of which average signal >50 could be used for further analysis. To each gene, maximum and minimum signal values were selected, and then divided between them. Only the genes of the division value >3 were selected and considered as differently expressed. All of the differently expressed genes were clustered by using MeV software.

To determine the relationship among fibroblasts and iOPC, brain-derived OPC and iOL cells, each sample was analyzed respectively. Data were filtered based on average signal and baseline was set as 50 to increase the sensitivity. Differently expressed genes were selected by 3 folds changed as threshold. To examine the potential OPC differentiation pathways relevant to the immortalization, all OPC differentiation genes from Gene Ontology Website (http://www.geneontology.org/, GO: 0030182) were compared with the microarray data. For gene enrichment analysis, inventors used web-based Gorilla program (http://cbl-gorilla.cs.technion.ac.il/).

Microarray data were quantile-normalized and filtered based on the average signal, and differently expressed genes were selected for further analysis. Hierarchical cluster analysis revealed a significant difference of gene expression profiles between iOPC cells and their parental fibroblasts (FIG. 4a), suggesting that iOPCs are clearly distinct from parental fibroblasts. Further, clustering analysis of global gene expression revealed that the transcription profile of ROCK inhibitor-induced iOPCs were tightly clustered with the transcription profile of human brain-derived OPCs and were distant from the profile of the parental fibroblasts (FIGS. 4a and b). By analysis of the 4-folds changed genes of the microarray data, iOPCs and brain-derived OPCs showed significant gene expression overlap for neural transcription factors (data not shown). For gene enrichment analysis, inventors found that particular markers of different germ layers were significantly changed in iOPCs, compared with those in parental fibroblasts (data not shown). Inventors also analyzed expressions of fibroblast specific genes during OPC conversion. Expressions of 68 fibroblast specific genes were significantly changed in iOPCs compared to the parental fibroblasts, whereas 51 out of 68 changed genes showed the same expression pattern between iOPCs and brain-derived OPCs. These data suggest that there may be permanent down-regulation of a set of fibroblast specific genes during OPC conversion. Taken together, these findings indicate that the genetic trans-differentiation erased the majority of the evident expression hallmarks of the cell of origin, whereas specifically inducing the OPC phenotype.

Example 6

To examine the in-vivo myelinating capacity of iOPCs, inventors implanted them in the demyelinated corpus callosum of cuprizone-fed mice. C57BL/6 mice were put on a diet of 0.2% (w/w) cuprizone (Sigma Aldrich), a copper chelator. This diet leads to selective oligodendrocyte death followed by demyelination of axons mainly in the corpus callosum. Feeding cuprizone diet for a longer term (>12 weeks) results in depletion of the pool of endogenous OPCs in the corpus callosum and finally leads to its complete demyelination. At 12 weeks after the start of the cuprizone diet, mice were divided into three groups one group (n=6) received a ROCK inhibitor iOPCs (7 D induction) in PBS and a second group (n=3) was given PBS only, and a third group (n=3) was injected with parental fibroblasts (n=3). On the day of transplantation, cells were harvested with accutase, counted, and resuspended at concentration of 25,000 cells/W. Four microliters of cell suspension was injected into corpus callosum of C57BL/6 mice using the following stereotactic co-ordinates (in reference to Bregma point): 10.98 mm (anterioposterior axis), 21.75 mm (lateromedial axis), 22.25 mm (vertical axis), suspensions of 100,000 cells in 4 W PBS were slowly injected into the corpus callosum of ketamine-anesthetized mice using a 10 W Hamilton injection syringe (22 s/200/3) (Hamilton, Reno, Nev., 80365). After the implantation of the iOPCs, mice were taken off the cuprizone diet and put back on normal diet to avoid degeneration of the implanted OPCs by cuprizone. Mice with implantation of iOPCs were perfusion fixated at 4 weeks for IHC analysis.

IHC analysis was performed as previously described. Briefly, mice were perfused transcardially with 4% PFA under isoflurane anaesthesia. Brains were excised and sectioned on a cryostat for immunohistochemical analysis of the cell implants. Implanted cells were identified by their inclusion of GFP. To analyze the differentiation of the implanted cells, the primary antibodies were used described in antibody section. Subsequently, various fluorescent secondary antibodies were used to visualize the specific primary immunoreaction product in single and double immunohistochemical stainings.

Immunohistochemistry revealed that only ~20% of the implanted cells survived (FIG. 5a). Surviving iOPCs developed into mature MBP-expressing OLs that contributed to the remyelination of the corpus callosum axons (FIG. 5b). Confocal microscopy revealed that MBP+ tube-like structures surrounded neurofilament-positive axons, indicating oligodendroglial ensheathment of host axons by the implanted iOPCs (FIG. 5c). No similar structures were observed in nontransplanted brains (parental fibroblasts or PBS injection, n=3 each; no injection of the left side, n=12). These results demonstrated that ROCK inhibitor induced OPCs can give rise to myelinating oligodendrocytes in vivo.

Example 7

To assess the general application of ROCK inhibitor for direct conversion of different neural cells, inventors tweaked the protocol for induction of iOPCs and successfully converted fibroblasts to typical neurons and astrocytes. using the following procedure:

at Day 1, coat tissue culture 24-well plate with 0.1 mg/ml Poly-L-ornithine solution (sigma, P4957) for at least 3 hours; wash wells 3 times with autoclaved MilliQ water, 5 mins each; add 500 ul/well of 2 µg/ml Fibronectin (sigma, F0556) and 10 µg/ml Laminin (ROCHE, 11243217001) solution in 1×PBS and place in incubator overnight to coat. At Day 2, aspirate the F/L solution from the well, wash with basic medium and plate fibroblast cells with basic medium at 2×10^4 cells per well. At Day 3, aspirate basic medium from the well, wash with PBS once, and feed cells with induction medium. From Day 6-10, when cells change their morphology into neural-like cells, culture cells with mature medium or OPC medium.

ROCK inhibitor-induced neurons and astrocytes showed cell type—specific morphology and biomarkers. For example, induced neuronal cells (iNCs) showed positive staining of neuronal biomarkers Tuj and MAP2 and neuron excitation (FIGS. 6 and 7); whereas induced astrocytes showed positive staining of astrocyte-specific biomarker, GFAP (FIG. 8). These results demonstrated the general applicability of ROCK inhibitor for induction of all kinds of neural cells, neurons, and glials, although further optimization will be needed for direct conversion of individual cell types.

In the specification, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing a neural cell, comprising:
culturing a differentiated non-neural cell with a first medium,
wherein the first medium consists of:
a first basic medium,
a protein kinase inhibitor,
brain-like neurotrophic factor (BDNF),
neurotrophin 3 (NT3),
valproic acid (VPA),
dibutyryl cyclic adenosine monophosphate (dbcAMP),
penicillin/streptomycin, and
Retinoic acid;
wherein the protein kinase inhibitor is at least one selected from the group consisting of ROCK inhibitor, AKT/mTOR inhibitor, PI3K inhibitor, FAK inhibitor and immunosuppressants.

2. The method of claim 1, further comprising:
culturing the cell with a second medium or a third medium after the culturing with the first medium,
wherein the second medium comprises:
a second basic medium,
a protein kinase inhibitor,
N2 cell culture medium additive (N-2),
B27 cell culture medium additives (B-27) without vitamin A,
Glutamax,
sonic hedgehog homolog (SHH),
fibroblast growth factor (FGF2),
platelet derived growth factor-AA (PDGF-AA), and
Retinoic acid;
the third medium comprises:
a third basic medium,
a protein kinase inhibitor,
N-2,
B-27 without vitamin A,
Glutamax,
SHH,
Noggin,
dbcAMP,
insulin-like growth factor (IGF),
NT3, and
Retinoic acid; and
wherein the protein kinase inhibitor of the second and the third medium is independently at least one selected from the group consisting of ROCK inhibitor, AKT/mTOR inhibitor, PI3K inhibitor, FAK inhibitor and immunosuppressants.

3. The method of claim 2, wherein the first basic medium is neuronal medium, the second basic medium is DMEM/F12 medium, the third basic medium is DMEM/F12 medium.

4. The method of claim 2, wherein the protein kinase inhibitor is at least one selected from the group consisting of Y27632, Palomid 529, LY294002, PF562271 and rapamycin.

5. The method of claim 2, wherein the first medium comprises:
5 μM-20 μM ROCK inhibitor (Y27632),
5 ng/ml-20 ng/ml BDNF,
5 ng/ml-20 ng/ml NT3,
0.5 mM-1.5 mM VPA,
25 μM-100 μM dbcAMP, and
0.5 μM-1 μM retinoic acid;
the second medium comprises:
5 μM-20 μM Y27632,
1×N-2,
1×B-27 without vitamin A,
1× Glutamax,
100 ng/ml-400 ng/ml SHH,
10 ng/ml-40 ng/ml FGF2,
10 ng/ml-40 ng/ml PDGF-AA, and
0.5 μM-1 μM retinoic acid,
the third medium comprises:
5 μM-20 μM Y27632,
1×N-2,
1×B-27 without vitamin A,
1× Glutamax,
100 ng/ml-400 ng/ml SHH,
50 ng/ml-200 ng/ml Noggin,
50 ng/ml-200 ng/ml dbcAMP,
50 ng/ml-200 ng/ml IGF,
5 ng/ml-20 ng/ml NT3, and
0.5 μM-1 μM retinoic acid.

6. The method of claim 5, wherein the first medium comprises:
10 μM Y27632,
10 ng/ml BDNF,
10 ng/ml NT3,
1 mM VPA,
50 μM dbcAMP, and
0.5 μM retinoic acid;

the second medium comprises:
10 μM Y27632,
1×N-2,
1×B-27 without vitamin A,
1× Glutamax,
200 ng/ml SHH,
20 ng/ml FGF2,
20 ng/ml PDGF-AA, and
0.5 μM retinoic acid;
the third medium comprises:
10 μM Y27632,
1×N-2,
1×B-27 without vitamin A,
1× Glutamax,
200 ng/ml SHH,
100 ng/ml Noggin,
100 ng/ml dbcAMP,
100 ng/ml IGF,
10 ng/ml NT3, and
0.5 μM retinoic acid.

7. The method of claim 1, wherein the neural cell is at least one selected from the group consisting of oligodendrocyte progenitor cell, mature oligodendrocyte, neuron and astrocyte.

8. The method of claim 1, wherein the differentiated non-neural cell is at least one selected from the group consisting of human cell, fibroblast cell, epithelial cell, adult cell and neonatal cell.

* * * * *